(12) United States Patent
Ait Si Selmi et al.

(10) Patent No.: US 12,208,024 B2
(45) Date of Patent: Jan. 28, 2025

(54) TRIALLING

(71) Applicant: DePuy Ireland Unlimited Company, Ringaskiddy (IE)

(72) Inventors: Tarik Ait Si Selmi, Lyons (FR); Sarah Bushell, Leeds (GB); Patrick Cannon, Warsaw, IN (US); Kristoff Corten, Herselt (BE); Phillip Lindeman, Warsaw, IN (US); John Bohannon Mason, Charlotte, NC (US); Jamie Olson, Warsaw, IN (US); Carol Wagner, Warsaw, IN (US); Duncan Young, Leeds (GB); Michael Brock, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 761 days.

(21) Appl. No.: 17/298,789

(22) PCT Filed: Nov. 27, 2019

(86) PCT No.: PCT/IB2019/060251
§ 371 (c)(1),
(2) Date: Jun. 1, 2021

(87) PCT Pub. No.: WO2020/115618
PCT Pub. Date: Jun. 11, 2020

(65) Prior Publication Data
US 2022/0031476 A1    Feb. 3, 2022

Related U.S. Application Data

(60) Provisional application No. 62/774,971, filed on Dec. 4, 2018.

(51) Int. Cl.
*A61F 2/46* (2006.01)
*A61F 2/30* (2006.01)
*A61F 2/36* (2006.01)

(52) U.S. Cl.
CPC .. *A61F 2/4684* (2013.01); *A61F 2002/30607* (2013.01); *A61F 2002/30617* (2013.01);
(Continued)

(58) Field of Classification Search
CPC ...... A61F 2002/3652; A61F 2002/3654; A61F 2/4684; A61F 2/3609; A61F 2002/30617
See application file for complete search history.

(56) References Cited

U.S. PATENT DOCUMENTS

| 5,746,771 A | 5/1998 | Clement, Jr. |
| 6,494,913 B1 * | 12/2002 | Huebner ............ A61B 17/1778 606/87 |

(Continued)

FOREIGN PATENT DOCUMENTS

| CN | 101883540 A | 11/2010 |
| JP | 2011512908 A | 4/2011 |

(Continued)

OTHER PUBLICATIONS

Chinese Office Action From Corresponding Chinese Application No. 201980080742.0, dated Nov. 1, 2023, 9 pages.

(Continued)

*Primary Examiner* — Javier G Blanco
(74) *Attorney, Agent, or Firm* — Barnes & Thornburg LLP (57) ABSTRACT

A neck trial (170) is disclosed. The neck trial has a body (182) and a neck (186). The body has an exterior surface. The neck extends away from the body along a neck axis (190). At least one first line (194) is provided on the exterior surface, which extends in a first direction parallel to an (Continued)

inferior-superior axis of a patient when in use. At least one second line (196) is provided on the exterior surface, which extends in a second direction parallel to a medial-lateral axis of the patient in use. The number of first lines, or the position of the first line or lines relative to the second line or lines, is indicative of an amount of offset in the medial-lateral direction caused by the neck trial. The number of second lines, or the position of the second line or lines relative to the first line or lines, is indicative of an amount of leg-length in the inferior-superior direction caused by the neck trial. A kit of parts, a trial assembly and a method of trialling a joint of a patient are also disclosed.

15 Claims, 8 Drawing Sheets

(52) U.S. Cl.
CPC ..... *A61F 2/3609* (2013.01); *A61F 2002/3625* (2013.01); *A61F 2002/4658* (2013.01); *A61F 2002/4668* (2013.01)

(56) References Cited

U.S. PATENT DOCUMENTS

| | | | |
|---|---|---|---|
| 8,491,664 B2 | 7/2013 | McMahon et al. | |
| 8,690,875 B2 | 4/2014 | Bergin et al. | |
| 9,381,096 B2 | 7/2016 | Davenport et al. | |
| 11,207,195 B2 | 12/2021 | Bushell et al. | |
| 11,344,436 B2 | 5/2022 | Butler et al. | |
| 2010/0249943 A1* | 9/2010 | Bergin | A61F 2/4684 623/22.42 |
| 2011/0093087 A1* | 4/2011 | Mcmahon | A61F 2/34 623/22.42 |
| 2011/0218642 A1* | 9/2011 | Widmer | A61F 2/4684 623/22.42 |
| 2013/0325132 A1* | 12/2013 | Reignier | A61F 2/4684 623/23.15 |
| 2015/0018961 A1 | 1/2015 | Huddle | |
| 2015/0313724 A1* | 11/2015 | Jackson, III | A61F 2/34 623/22.12 |
| 2016/0030199 A1* | 2/2016 | Hunt | A61F 2/3662 623/23.42 |
| 2016/0030200 A1 | 2/2016 | Hunt et al. | |

FOREIGN PATENT DOCUMENTS

| | | |
|---|---|---|
| WO | 2013/117909 A1 | 8/2013 |
| WO | 2014140636 A1 | 9/2014 |
| WO | 2017097760 A1 | 6/2017 |
| WO | 2018189125 A1 | 10/2018 |

OTHER PUBLICATIONS

Japanese Search Report From Corresponding Japanese Application No. 2021-531736, dated Sep. 22, 2023, 5 pages.
PCT/IB2019/060251 International Search Report dated Feb. 20, 2020.
Japanese Office Action From Corresponding Japanese Application No. 2021-531736, dated Sep. 23, 2023, 5 pages.

* cited by examiner

A = Offset
B = Leg Length
C = Neck Length

TRIALLING

CROSS-REFERENCE TO RELATED APPLICATIONS

This application is a National Stage Application filed Under 35 U.S.C. § 371 of International Application No. PCT/IB2019/060251 filed Nov. 27, 2019, which claims priority to U.S. provisional 62/774,971 filed Dec. 4, 2018, which are both hereby incorporated by reference in their entireties.

FIELD OF INVENTION

The present invention relates generally to apparatus and methods for use in surgery and in particular to trial components, kits of trial components and methods of trialling which may be used in surgery.

BACKGROUND OF THE INVENTION

Some surgical procedures which involve the replacement of a part of the body with a prosthetic component may use trial components during a trialling stage of the surgical procedure. Trial components may be used to help determine the actual prosthetic components to use and/or the positioning and/or orientation of the actual prosthetic components so as to try and attain some intended surgical outcome. Trial components are generally used to help the surgeon understand the selection of the final implant before committing to the final prosthetic implant. The use of trial components can also help avoid any damage or fouling of the actual prosthetic components that might otherwise occur if one or more prosthetic components were used instead for trialling.

A range of trial components of different shapes and/or sizes and/or geometries may be used so that the surgeon can try and determine which prosthetic component to use. However, it can be difficult for the surgeon to understand the effects on the surgical outcome that a particular trial component may have compared to one or more other trial components. While a trial component may improve one aspect of the surgical outcome, it may have a negative impact on another aspect of the surgical outcome Sometimes, multiple trial components may be combined into a trial construct which can exacerbate this.

Furthermore, when a trial or trail construct is in place in the patient's body, it can be hard to visually inspect the trial or trial construct to understand exactly which trial or trial construct is currently being used and how that may impact on the surgical outcome. This is particularly the case for minimally invasive surgical procedures for which visual access to the surgical site may be very limited.

Therefore trial components, kits of trial components and/or methods of trialling which make it easier for the surgeon to understand that likely impact of a particular trial or trials on the outcome of a surgical procedure would be beneficial.

SUMMARY OF THE INVENTION

A first aspect of the invention provides a neck trial comprising: a body having an exterior surface; and a neck extending away from the body and along a neck axis, wherein at least one first line is provided on the exterior surface and the or each first line extends in a first direction parallel to an inferior-superior axis of a patient when in use and at least one second line is provided on the exterior surface and the or each second line extends in a second direction parallel to a medial-lateral axis of the patient in use, and wherein: the number of first lines, or the position of the first line or lines relative to the second line or lines, is indicative of an amount of offset in the medial-lateral direction caused by the neck trial; and the number of second lines, or the position of the second line or lines relative to the first line or lines, is indicative of an amount of leg-length in the inferior-superior direction caused by the neck trial.

The number of first lines may be in the range from 1 to 3, and preferably may be in the range from 1 to 2.

The number of second lines may be in the range from 1 to 3, and preferably may be in the range from 1 to 2.

The number of first lines may be greater than one and/or the number of second lines may be greater than one.

Each line may be a solid line.

Each line may be printed or a marking.

Each line may be a structural formation. The or each structural formation may be a male formation, for example a rib or ridge, or a female formation, such as a groove or trough.

All of the first lines and the second lines may be adjacent and/or may be positioned on the same part of the external surface.

All of the first lines and second lines may be on an anterior facing surface and/or a posterior facing surface of the neck trial in use.

The or each first line may be separate to the or each second line. There may be a gap or discontinuity between the or each first line and the or each second line.

The or each first line may be connected to the or each second line.

The or each first line may be positioned medially to the or each second line. The or each first line may be connected to a medial end of the or each second line.

The or each first line may be positioned laterally to the or each second line. The or each first line may be connected to a lateral end of the or each second line.

The or each second line may be positioned superiorly to the or each first line. The or each second line may be connected to a superior end of the or each first line.

The or each second line may be positioned inferiorly to the or each first line. The or each second line may be connected to an inferior end of the or each first line A second aspect of the invention provides a kit of parts comprising a plurality of neck trials according to the first aspect of the invention, wherein each neck trial has a different number of first lines and/or a different number of second lines.

A second aspect of the invention also provides a kit of parts comprising: a plurality of neck trials according to the first aspect, wherein each neck trial has a different position of the first line or lines relative to the second line or lines and/or a different position of the second line or lines relative to the first line or lines.

The kit of parts may further include a head trial which is releasably attachable to each of the neck trials and having a head line extending in a plane perpendicular to the neck axis when releasably attached to a one of the neck trials.

The kit of parts may further include a plurality of head trials, each being releasably attachable to each of the neck trials and each having a different number of head lines extending in a respective plane perpendicular to the neck axis when releasably attached to a one of the neck trials, and wherein each head trial is releasably attachable to the one of the neck trials at a different position along the neck axis.

The number of head lines on each head trial may be indicative of the distance along the neck axis of the trial head from the neck trial when the head trial is releasably attached to the neck trial in use.

The kit of parts may further include a liner trial, wherein the liner trial has a rim defining a mouth of the liner trial for accepting the head trial in use, and wherein at least one liner line extends in a plane parallel to the mouth and wherein the number of liner lines indicates the distance by which the trial liner moves the head trial along the neck axis.

The liner line may be on an exterior surface of the liner trial adjacent the mouth.

The kit of parts may further comprise a plurality of liner trials, each liner trial having a different number of liner lines, each liner line extending in a respective plane parallel to a respective mouth.

The kit of parts may further include an augmented liner trial, wherein the augmented liner trial has a portion of a rim defining a mouth of the augmented liner trial for accepting the head trial in use, and wherein a liner line extends in a plane parallel to the mouth.

The or each liner trial and the or each head trial may have the same colour.

The or each liner trial may have an inner diameter and the or each head trial may have an outer diameter and wherein the inner diameter and the outer diameter match such that the head trial can articulate within the liner trial.

The kit of parts may include two different neck trials, or five different neck trials of seven different neck trials.

The kit of parts may include two different liner trials or three different liner trials.

The kit of parts may include six different head trials.

A third aspect of the invention provides a trial assembly, comprising: a neck trial according to the first aspect; and a head trail, wherein the head trial which is releasably attached to the neck trial and has at least one head line, the or each head line extending in a respective plane perpendicular to the neck axis, and wherein the number of head lines is indicative of the length of the trial assembly along the neck axis.

The trial assembly may further comprise: a liner trial, wherein the liner trial has a rim defining a mouth of the liner trial, the head trial being accepted in the mouth, and wherein a liner line extends in a plane parallel to the mouth.

A fourth aspect of the invention provides a method of trialling a joint of a patient, comprising: assembling a trial joint assembly, the trial joint assembly including a neck trial and a head trial, the trial neck bearing a plurality of lines arranged to indicate an amount of offset in a medial-lateral direction of the patient and an amount of leg-length in an inferior-superior direction of the patient arising from the neck trial; reducing a trial joint of the patient including the trial joint assembly; assessing the behaviour of the trial joint; and inspecting the plurality of lines to determine any changes to prosthetic components to be implanted in the patient to reconstruct the joint of the patient.

Any one or more of the trial joint components of the first aspect or kits of parts of the second aspect or trial assembles of the third aspect may be used in the method. These may give rise to corresponding counterpart method features.

The head trial may include at least one head line, the or each head line extending in a respective plane perpendicular to a neck axis of the neck trial, and the method may further comprise also inspecting the number of head lines to determine any changes to prosthetic components to be implanted in the patient to reconstruct the joint of the patient.

The trial joint may further include a liner trial, wherein the liner trial has a rim defining a mouth of the liner trial in which the head trial is accepted, and wherein the liner trial includes at least one liner line, the or each liner line extending in a respective plane parallel to the mouth, and the method may further comprise: also inspecting the number of liner lines to determine any changes to prosthetic components to be implanted in the patient to reconstruct the joint of the patient.

Assessing the behaviour of the trial joint may include assessing a resulting off-set in the medial-lateral direction.

Assessing the behaviour of the trial joint may include assessing a resulting leg length in the inferior-superior direction.

Assessing the behaviour of the trial joint may include assessing a resulting soft tissue tension of the trial joint.

The method may further comprise any one or more of: separating the trial joint; selecting a different neck trial and/or head trial and/or liner trial, based on the lines on each of them; reducing a further trial joint using the selected trial component or components in place of the corresponding previous trial component or components; assessing the behaviour of the further trial joint; and inspecting the plurality of lines on the components of the further trial joint to determine any changes to prosthetic components to be implanted in the patient to reconstruct the joint of the patient.

Assessing the behaviour of the trial joint or further trial joint may include assessing the range of motion of the trial joint or further trial joint.

Further aspects of the invention are provided by each of the liner trial, head trial and neck trial components individually.

Further aspect of the invention are provided by any combination of the liner trial, head trial and neck trial components and also in kit form or assembled form.

Further aspects of the invention are provided by methods of use of each of the liner trial, head trial and neck trial components individually or in any combinations thereof.

BRIEF DESCRIPTION OF THE FIGURES

Embodiments of the invention will now be described in detail, and by way of example only, and with reference to the accompanying drawings, in which.

Similar items in the different Figures share common reference signs unless indicated otherwise.

DETAILED DESCRIPTION OF EMBODIMENTS

Embodiments of the invention will be described within the context of orthopedics and in particular in relation to a hip joint. However, it will be appreciated that the invention is not necessarily limited in application to hip joints and may also be used in other ball and socket type joints.

As explained in greater detail below, one or more vertical lines (i.e. parallel to the inferior-superior axis of the patient's body in use) may be used to represent an amount of tension introduced into the joint owing to movement of the patient's limb along the medial-lateral axis, and which may be referred to as limb offset. Movement of the limb relative to the body in the medial direction will generally decrease tension and movement of the limb relative to the body in the lateral direction will generally increase tension. One or more horizontal lines (i.e. parallel to the medial-lateral axis of the patient's body in use) are used to represent an amount of tension introduced into the joint owing to movement of the patient's limb along the inferior-superior axis, and which may be referred to as limb length. Movement of the limb relative to the body in the superior direction will generally decrease tension and movement of the limb relative to the body in the inferior direction will generally increase tension. One or more diagonal lines (which may be generally perpendicular to the neck axis in use) may be used to represent an amount of tension introduced into the joint owing to movement of the patient's limb (arm or leg) along both the medial-lateral axis and the inferior-superior axis.

In the following, the "line" or "lines" will generally be used to indicate any linear indicium or linear indicia which can be discerned by a user. The line may have various forms, e.g. solid, broken, chain, etc. and may be embodied in various ways, e.g. by printing or marking or similar, and/or by various physical features, e.g. ridges, ribs, groove or channels or similar. Hence, although line will be used below for the sake of clarity, it will be appreciated that any linear indicium or indicia may be used in practice.

Figure 1A:
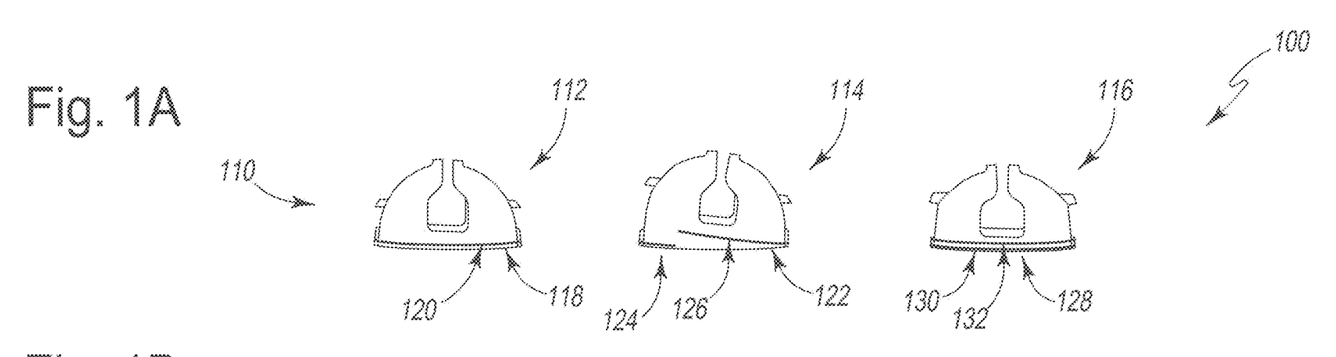
FIGS. 1A to 1C show components of a kit of trials according to an aspect of the invention and including various trial components each according to an aspect of the invention.
Figures 1B, 1C:
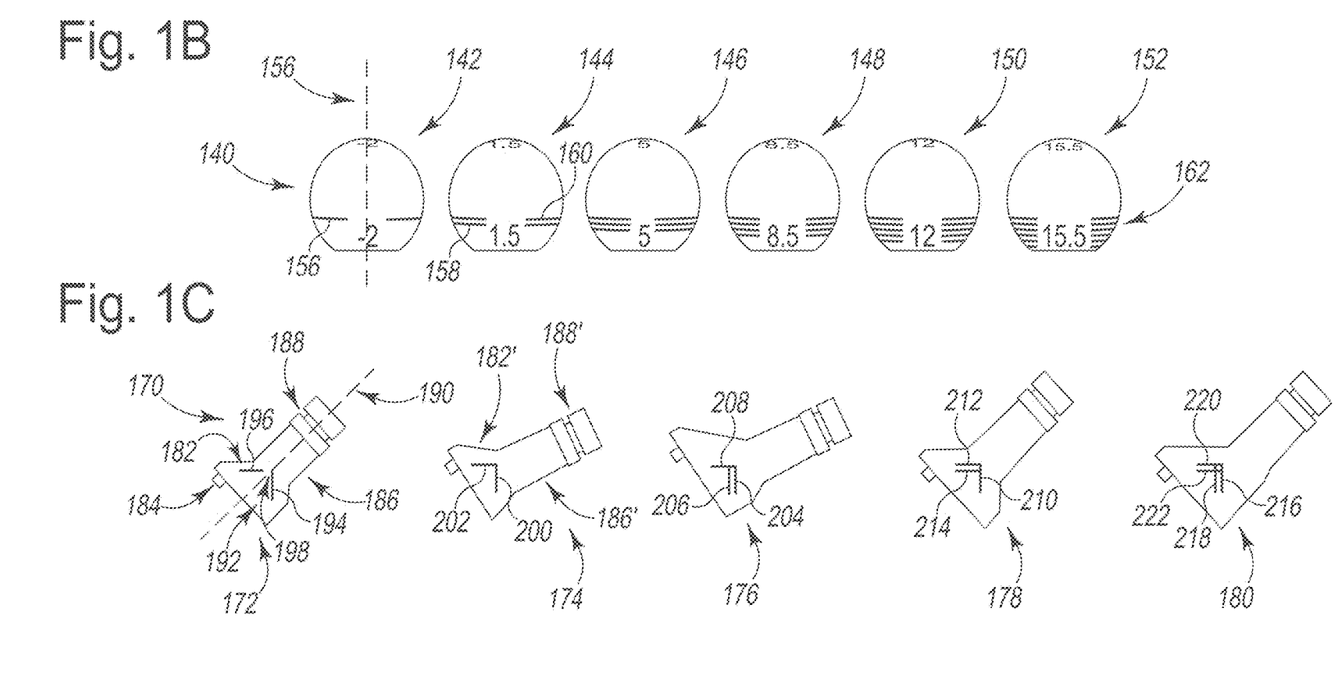

With reference to FIGS. 1A to 1C, there is shown a kit of parts 100 according to an embodiment of the invention. The kit of parts 100 comprises a plurality of different types of trial component which can be used during a trialling stage of a surgical procedure, such as a hip replacement procedure. The kit of parts 100 can be provided as a trialling kit within a tray which can be provided to the operating theatre staff for use during the surgical procedure. The kit of parts 100 illustrated in FIGS. 1A to 1C is for a particular head size or diameter. A similar kit of parts can be provided for other different head diameters. Also, the kit of parts 100 is for a particular implant system having a particular set of necks and neck geometries. A similar kit of parts can be provided for other different implant systems having a different neck or set of necks.

As illustrated in FIG. 1A, the trialling kit 100 may include one or a plurality of liner trials 110. Three different liner trials 112, 114 and 116 are provided. Each liner trial includes one or more lines as described in greater detail below. A first liner trial 112 has a body with a rim 118 defining a generally hemispherical cavity in which a head trial can be received in use. The circular rim 118 extends around and defines a mouth of the liner trial. A line, in the form of a solid line 120, is provided on an outer surface of the liner trial and extends around the periphery of the mouth, adjacent and parallel to the plane of the rim 118. The first liner trial 112 has a minimal or smallest thickness of the liner trials 110 provided in the kit. The thickness of the first liner trial 112 may correspond to an increase in overall neck length of approximately 2 mm.

The second liner trial 114 is generally similar to the first liner trial 112. However, the second liner trial 114 is an augmented liner trial which has a further segment 124 extending away from the rim 122 so as to define a slightly greater than hemispherical cavity within the liner trial 114. This augmented liner trial 114 may be used in circumstances in which the trial cup has been placed with a relatively vertical orientation i.e. without much inclination relative to the patient's pelvis. Hence, the segment 124 helps to avoid dislocation of the head. The second liner trial 114 also includes a single line 126 on an outer surface and extending around the mouth of the liner trial and adjacent and generally parallel to the plane of the rim 122. The second liner trial 114 has generally the same thickness as the first liner trial 112. Hence, the thickness of the second liner trial 114 may correspond to an increase in overall neck length of approximately 2 mm.

The third liner trial 116 is generally similar to the first liner trial 112 and also includes a rim 128 extending around a mouth of hemispherical cavity defined by the body of the liner trial 116. However, liner trial 116 includes a first line 130 and a second line 132, each in the form of a solid line. Liner trial 116 has a greater thickness than the first 112 and second 114 liner trials. Hence, when inserted in a trial cup, the third liner trial 116 modifies the position of the centre of rotation of the joint in a direction away from the pelvis in both the lateral and inferior directions, and generally along the neck axis compared to the first or second liner trials.

In other embodiments, the liner trial 116 may be adapted otherwise to modify the position of the centre of rotation along the neck axis. For example, rather than having a different thickness, other features of the liner trial may be modified in order to change the position of the centre of rotation of a head trial in use. For example, third liner trial 116 may move the centre of rotation approximately 2 mm further along a cup axis (defined by a line passing through the centre of the mouth of the cup and liner and perpendicular to the plane of the mouth of the liner and cup), compared to the first and second liner trials. Hence, the thickness of the third liner trial 116 may corresponds to an increase in overall neck length of approximately 4 mm.

Hence, each liner trial includes at least one line and the number of lines on any liner trial is proportional to, or otherwise corresponds to, an amount of distance introduced into the trial joint assembly, and corresponding tension in the trial joint assembly, by use of that liner trial in the trial joint assembly.

Each of trial liners 112, 114, 116 defines a generally hemispherical cavity having an inner diameter of approximately 32 mm, for example. The trialling kit 100 also includes a plurality of head trials 140 as illustrated in FIG. 1B. In the illustrated embodiment, six head trials 142, 144, 146, 148, 150, 152 are provided. Each head trial has a generally truncated spherical form and has the same outer diameter of approximately 32 mm. Hence, each of head trials 142 to 152 can be received in any respective one of the liner trials 112, 114, 116 of the kit.

The liner trials and head trials of FIG. 1, therefore correspond to a first size. A plurality of sets of liner trials and head trails can be provided, with each set corresponding to a different size. For example, liner trial inner diameters and head trial outer diameters of approximately 22 mm, 28 mm, 32 mm, 36 mm and 40 mm may be provided for corresponding sized prosthetic components. As will be appreciated from the following, the same neck trials can be used with liner trials and head trials of different sizes.

The body of each head trial defines a respective cavity therein for receiving a free end of a neck trial. Each cavity extends generally along a head axis, e.g. 154, which passes through the centre of the head trial, and generally perpendicularly to a flat underside thereof and through a pole of the head trial.

Each of the head trials 142 to 152 is generally similar other than the position along the head axis 154 of the respective cavities is different for each of the head trials so that the centre of rotation of each head trial can adopt a different position along the neck axis when assembled on a neck trial in use. Also, each head trial includes a different number of lines and the number of lines is proportional to, or otherwise corresponds to, the resulting position along the neck axis arising from the position of the cavity within the head trial. Hence, each head trial includes at least one line and the number of lines indicates the amount by which the trial joint assembly will change along the neck axis, and with a corresponding change in soft tissue tension, owing to use of that head trial in the trial joint assembly.

For example, the first head trial 142 has a single line 156 generally in the form of a solid line extending at least partially around the head axis 154 and in a plane generally perpendicular to the head axis 154. This first head trial 142 corresponds to a smallest neck length which may be less than a normal or default neck length and hence can be used to reduce an overall neck length in use.

A second head trial 144 includes first and second lines 158, 160 and has a cavity arranged to position the centre of rotation of head trial 144 further away from the neck trial along the neck axis when assembled thereon in use compared to the first head trial 142. For example, the difference in position along the neck axis between the first head trial 142 and second head trial 144 may be approximately 3.5 mm. Similarly, each of the third, fourth, fifth and sixth head trials have an incremental number of lines and each have respective cavities configured to position the centre of rotation of the head trial further along the neck axis and away from the neck trial. For example, the sixth head trial 152 has six lines 162 and corresponds to the greatest neck length which may be approximately 17.5 mm longer than a corresponding neck length arising from use of a first head trial 142 on the same neck trial.

It will be appreciated that each line does not need to correspond to the same change in neck length. For example, each additional line may not correspond to a same 3.5 mm change in neck length. Rather, the amount of the change in neck length may vary for addition or omission of a line. It is simply that the number of lines indicates or corresponds to the change in the neck length resulting from use of that particular trial head. The greater the number of lines, the greater the neck length and the fewer the number of lines, the less the neck length.

As noted above, each head trial has the same outer diameter and the outer diameter of each head trial matches the inner diameter of each of the liner trials so that any one of head trials 140 to 152 can be used with any one of liner trials 112 to 116. This compatibility between the head trials and liner trials can be indicated by making the colour of the head trials and the colour of the liner trials the same. For example, 22 mm diameter liner trials and head trials may all be tan coloured, 28 mm diameter liner trials and head trials may all be green coloured, 32 mm diameter liner trials and head trials may all be blue coloured, 36 mm diameter liner trials and head trials may all be orange coloured and 40 mm diameter liner trails and head trials may all be pink coloured.

Hence, for a particular size of head, the compatibility between the head trials and liner trials may be indicated by the head trials and liner trials all having the same matching colour.

In some embodiments, the head trials and the liner trials may be made from suitable plastics and polymers such as Polyphenylsulfone (PPSU) or Polyoxymethylene (POM) or similar.

A trialling kit for a different sized head may include similar components but having different inner and outer diameters and each of the head trials and liners trials for the second trialling kit may have a matching colour different to the matching colour of the first trialling kit. It will be appreciated that typically a reasonable number of different sized heads may be provided by an orthopedics manufacturer (for example approximately five different sized femoral heads of approximately 22 mm, 28 mm, 32 mm, 36 mm and 40 mm) and each trialling kit for each head size may have its own colour which matches within the kit but differs between kits, as described above.

The trialling kit 100 also includes a plurality of neck trials 170 as illustrated in FIG. 1C. In the embodiment illustrated in FIG. 1C, the trialling kit 100 includes five neck trials 172, 174, 176, 178 and 180. Each neck trial has a generally similar overall construction but a different geometry.

For example, with reference to the first neck trial 172, each neck trial has a body 182 with a male formation 184 extending from an underside thereof. A neck portion 186 extends away from the body 182 and along a neck axis 190. A taper 188 is provided at a free end of the neck 186 for releasably attaching a head trial thereto in use. The first neck trial has a neck-stem angle of approximately 135°.

First neck trial 172 is illustrated in FIG. 1C so as to form a part of a right hand hip joint in use. Hence, surface 192 is a generally anterior facing surface of the neck trial 172. Anteriorly facing surface 192 bears a first line 194 and a second line 196, each of which is in the form of a solid line.

The first line 194 is arranged to extend in a first direction generally parallel to the inferior-superior axis of a patient's body in use. The second line 196 is arranged to extend generally parallel to the medial-lateral axis of a patient's body in use.

The first line 194 indicates the extent to which the neck trial 172 will change the medial-lateral offset of the patient's leg. The second line 196 indicates the extent to which the neck trial 172 will change the leg length of the patient in use. As illustrated in FIG. 1C, the first neck trial 172 has only a single first line 194 and a single second line 196. The single second line 196 indicates that this trail neck 172 provides the minimal amount of change in the leg length of the patient in use.

As also illustrated in FIG. 1, there is a gap 198 between a superior the end of the first line 194 and a medial end of the second line 196. The gap 198 signifies the position of the first line 194 relative to the second line 196 and in particular that the first line 194 is positioned more medially than the medial end of the second line 196. This arrangement of the first line 194 relative to the second line 196 signifies or indicates that the first neck trial 172 will result in the minimal medial-lateral distance. In particular, the gap 198 signifies that the first neck trial 172 will provide a smaller media-lateral offset than a second neck trial 174. In particular, the first neck trial will move the limb approximately 5 mm in the medial direction along the medial-lateral axis relative to the pelvis.

Second neck trial 174 is generally similar to first neck trial 172 except that the position of its neck 186' relative to its body 182' is different such that the position of the taper 188' will move the limb relative to the pelvis further in the lateral direction compared to the first neck trial 172. The neck-stem angle for the second neck trial 174 is approximately 125°. As can be seen in FIG. 1C, the superior end of the first line 200 is connected to the medial end of the second line 202 and the absence of the gap 198 compared to the first neck trial 172, signifies that the second trial neck 174 will result in a greater offset in the lateral direction, approximately 5 mm, compared to the first trial neck 172.

The second neck trial 174 can be considered a neutral neck trial. In that case, the first neck trial 172 can be considered a reduced off-set neck trial as the first neck trial 172 will move the femur medially, by approximately 5 mm, compared to the second neck trial 174.

Further, the anterior facing surface of the second neck trial 174 includes one second line 202 parallel to the medial-lateral axis similarly to the first neck trial 172 and at the same position on the body 182' of the second neck trial as the second line 196 on the body 182 of the first neck trial 172. This combination and configuration of lines indicates that the second neck trial 174 provides the same leg length position as the first neck trial 172, but increases the medial-lateral offset of the leg (in the lateral direction) compared to the first neck trial 172.

The connected single first line 200 and single second line 202 may be used to indicate that the second neck trial is a neutral neck and hence positions the femur at a neutral leg-length and a neutral medial-lateral position. This may correspond to a standard or default neutral leg position for a surgical procedure.

For example, the second neck trial 174 may increase the medial-lateral offset, in the lateral direction by approximately 5 mm, compared to the first neck trial 172. Further, the second neck trial 174 has a slightly reduced neck-stem angle, compared to the first neck trial 172. The first neck trial 172 may have a neck stem angle of approximately 135° whereas the second neck trial 174 has a smaller neck-stem angle of approximately 125°.

The third neck trial 176 is generally similar to the first and second neck trials other than the neck is arranged relative to its body to position the leg relative to the pelvis further laterally along the medial-lateral axis of a patient in use, compared to the first and second neck trials. The third neck trial 176 may have a stem-neck angle of approximately 125°, similarly to the second neck trial, but be a high-offset neck trial. The third trial neck results in a femur positioned approximately 7 mm more laterally in the medial-lateral direction than the second trail neck 176. This further increase of the resulting medial-lateral offset of the patient's femur arising from the third neck trial 176 is represented by the presence of two first lines 204, 206 generally parallel to the superior-inferior axis on the anteriorly facing surface. Again, there is only a single second line 208 indicating that the third neck trial neck does not result in a chance of the leg-length compared to the first neck trial 172 or the second neck trial 174. The first first line 204 has the same position on the anterior surface as the first line 200 of the second neck trial, whereas the second first line 206 is more laterally positioned on the anterior surface of the third neck trial compared to the first line 200.

Fourth neck trial 178 is generally similar to second neck trial 174 except that the neck portion is arranged relative to the body portion to move the leg more inferiorly relative to the pelvis along the inferior-superior axis than the first, second or third neck trials. The fourth neck trial may have a stem-neck angle of approximately 135° and may move the leg approximately 5 mm inferiorly compared to the first to third neck trials. This is indicated by the presence of a single first line 210 and a first 212 and a second 214 second line on the anteriorly facing surface. The first second line 212 has the same position on the anterior face of the fourth neck trial as the first second line 298 on the third neck trial, whereas the second second line 214 is positioned more inferiorly on the fourth neck trial compared to the first second line 208 on the third neck trial. The fourth neck trial will result in the same medial-lateral position of the leg as the second neck trial 174 as indicated by the single first line 210.

The fifth neck trial 180 is generally similar to the fourth neck trial 178 other than the neck being arranged relative to the body so as to increase the medial-lateral offset of the femur in the lateral direction compared to the second and fourth neck trials. The fifth neck trial may have a stem-neck angle of approximately 135°. The resulting leg position in the inferior-superior direction is the same as for the fourth neck trial, i.e. approximately 5 mm more inferior, as indicated by the first 220 and second 222 second lines, and which have the same position on the anterior face of the fifth neck trial as lines 212 and 214 on the fourth neck trial. The amount of lateral offset in the medial-lateral direction is indicated by the presence of first 216 and second 218 first lines generally parallel to the superior-inferior axis and similarly to the third neck trial 176. Hence, the fifth neck trail may move the femur approximately 7 mm laterally and 5 mm inferiorly compared to the second neck trial 174.

The second neck trial 174 (having a stem-neck angle of approximately) 125° may be taken as a reference or neutral which provides a neutral or first amount of off set and a neutral or first amount of leg length. Compared to the second neck trial, the first neck trial 172 (having a stem-neck angle of approximately) 135° may move the leg approximately 5 mm medially, as reflected by the gap between, and relative position of, the vertical line 194 and the horizontal line 196 compared to the connected vertical line 200 and horizontal line 202 on the second neck trial, and does not change the leg length as reflected by the single horizontal line 196, 202 on each of them and at the same position on the anterior faces.

Compared to the second neck trial 174, the third neck trial 176 (having a stem-neck angle of approximately) 125° may move the leg approximately 7 mm laterally, as reflected by the two vertical lines 204, 206 compared to the one vertical line 200 on the second neck trial 174, and does not change the leg length as reflected by the single horizontal line on each of them. Hence, in this example, the second vertical line 206 on the third trial 176 indicates a change of 7 mm laterally compared to the second neck trial 174, whereas the gap and relative positions of the vertical line 194 and horizontal line 196 on the first neck trial 172 corresponds to a change of 5 mm medially compared to the second neck trial.

Compared to the second neck trial 174, the fourth neck trial 178 (having a stem-neck angle of approximately) 135° may move the leg approximately 5 mm inferiorly along the inferior-superior axis, as reflected by the two horizontal lines 212, 214 compared to the one horizontal line 202 on the second neck trial 174, and does not change the leg length as reflected by the single vertical line on each of them.

Compared to the second neck trial 174, the fifth neck trial 180 (having a stem-neck angle of approximately 135°) may move the leg approximately 5 mm inferiorly along the inferior-superior axis, as reflected by the two horizontal lines 220, 222 compared to the one horizontal line 202 on the second neck trial, and also moves the leg approximately 7 mm laterally as reflected by the two vertical lines 216, 218 on the fifth neck trial compared to the one vertical line 200 on the second neck trial 174.

Hence, the number of lines and/or relative position of the lines, is generally proportional to or corresponds to the change in the position of the leg (the more lines, the greater the change, the fewer lines the less the change). Each line, or relative position, may not corresponds to the same amount of change. For example the second vertical line 206 on the third neck trail corresponds to a change of 7 mm, compared to the second neck trial, whereas the gap 198 on the first neck trial 172 corresponds to a change of 5 mm compared to the second neck trial 174.

The same arrangements of linear indicia may be provided on the posteriorly facing surface of the neck trials as illustrated in FIG. 1C. Hence, those markings may be used when the neck trials are used for a left hand hip joint.

Figure 1D:
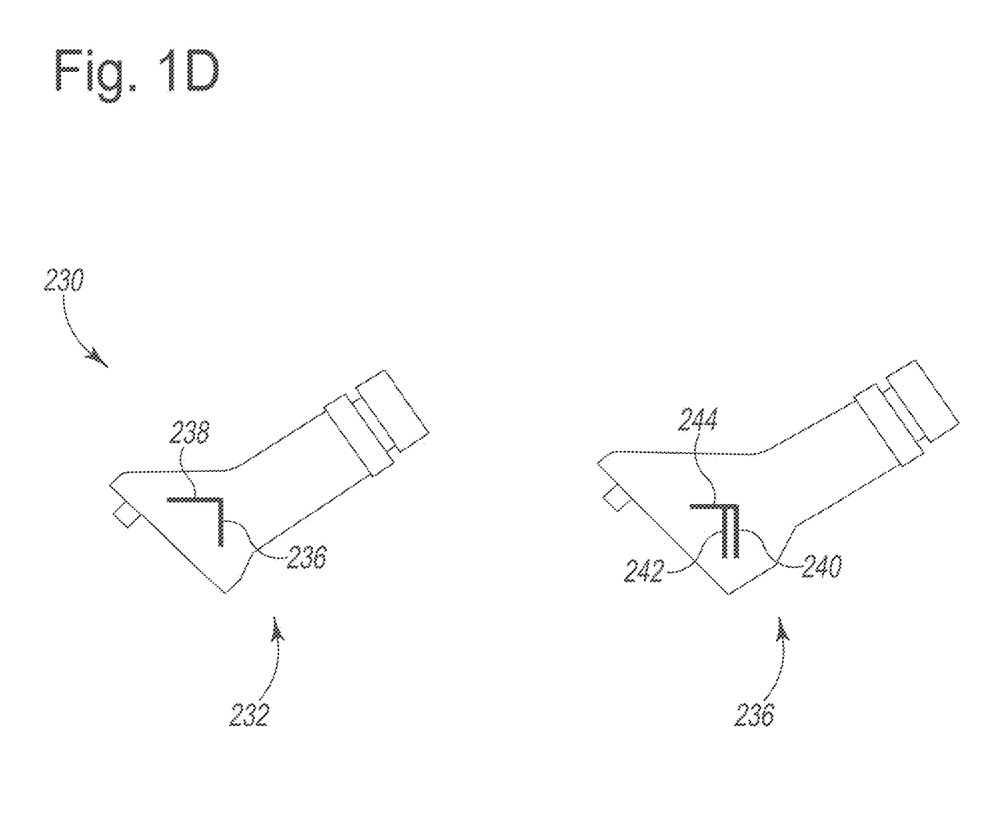
FIG. 1D shows a kit of neck trials, also according to an aspect of the invention, and additional, or alternative, to the neck trials shown in FIG. 1C.

FIG. 1D shows a further set of neck trials 230 which may be provided additionally or alternatively to the neck trials 170 illustrated in FIG. 1C. For example, neck trials 230 may correspond to a different implant system to that of neck trials 170 and hence may be used instead of neck trials 170 with the liner trials 110 and head trials 140 shown in FIGS. 1A and 1B.

The further neck trials 230 comprise a first neck trial 232 and a second neck trial 234 which are generally similar to those shown in FIG. 1C. First neck trail 232 and second neck trail 234 each have the same stem-neck angle of approximately 130°. First neck trial 232 includes a single vertical line 236 and a single horizontal line 238 and second neck trial 234 has a two vertical lines 240, 242 and a single horizontal line 244. Similarly to above, the single horizontal line on each neck trial indicates that each neck trial results in the same leg position along the inferior-superior axis, whereas the two vertical lines 240, 242 compared to the single vertical line 236 indicates that the second neck trial 234 results in a greater offset of the leg laterally compared to the first neck trial 232.

For example, the first neck trial 232 can be considered a neutral neck trial which has a standard off set positon of the leg as reflected by the single vertical line, whereas the second neck trial 234 can result in a high offset position as it moves the leg laterally, e.g. by approximately 4 mm to 8 mm, compared to the first trial neck 232.

An implant system may provide a different sizes of prosthesis and a pair of neck trials 232, 234 may be provided corresponding to the smaller sized prostheses and the larger sized prostheses. For example, for a first implant system, the second neck trial 234 for the smaller sized prostheses may move the leg 6 mm laterally whereas the second neck trial 234 for the larger sized prostheses may move the leg 8 mm laterally. For example, for a second implant system, a pair of neck trails 232, 234 may be provided for each of five different sizes of prostheses, and the lateral movement provided by the second neck trial 234 may be 4 mm, 5 mm, 6 mm, 7 mm and 8 mm for the smallest to the largest of the five sizes of prostheses.

The neck trials may be made from any suitable material, such as surgical grade stainless steel or various suitable polymers such as Polyetheretherketone (PEEK), or Polyaryletherketone (PAEK) or similar. The linear indicia may be provided on the anterior and/or anterior facing surfaces of the neck trials using laser marking.

The lines or linear indicia can be provided on the various trials as simple and high contrast markings which are easy to visualise by a user in order to understand the effect of the trial components on the trial joint assembly. The colour of the liners and/or heads can also be used to encode and communicate size information to the user.

Figure 2:
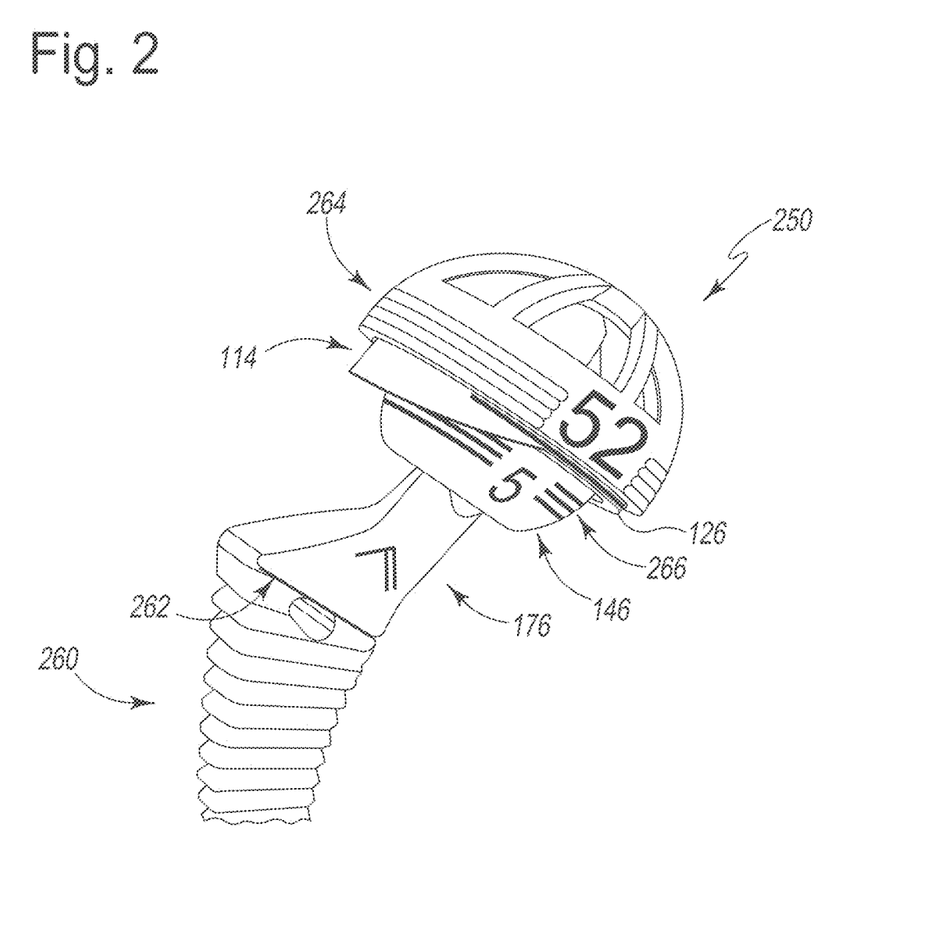
FIG. 2 shows a perspective view of a trial joint including a trial assembly of trial components from the kit of parts shown in FIGS. 1A to 1C and according to an aspect of the invention.

FIG. 2 shows a perspective view of an example trial hip joint 250 that may be constructed using a selection of the trial components illustrated in FIGS. 1A to 1C. The trial hip joint 250 includes a final broach 260 which has been used to prepare a femoral cavity within the femur of the patient. It will be appreciated that in other embodiments, other femoral parts may be used instead of a femoral broach. For example, a trial femoral stem may be used. In other embodiments, a prosthetic femoral stem may be used. Also, other instruments and/or tools used during preparation of the femur may be used instead.

The third neck trial 176 is releasably mounted on a proximal surface 262 of femoral broach 260. The proximal surface 262 has an aperture for receiving the male member 184 extending from the distal surface of the neck trial 176. In other embodiments, a male member may be provided on the proximal surface 262 to be received within a corresponding female formation within the body of the neck trial 176. The third head trial 146 is releasably attached to the taper of the neck trial 176. The head trial 146 is received within the cavity defined by the body of the augmented liner trial 114. The augmented liner trial 114 is received within a trial acetabular cup 264 which may be provided in the form of a shell as illustrated in FIG. 2. In other embodiments, the liner trial 114 may be received in the prosthetic shell or cup.

As discussed above, each of the trial components of the trialling kit 100 includes a number of lines or linear indicia and the number of lines or linear indicia, and/or the relative position of the horizontal and vertical lines, visually indicates the effect of each trial component on a particular property of the resulting joint. The linear indicia are a visual representation or indication of both the amount and direction of tension which is being applied to the resulting joint by each of the trail components in the trial joint assembly.

As illustrated in FIG. 2, the line 126 on augmented trial liner 114 is visible as are the three lines 266 on the head trial 146. Each of these are generally perpendicular to the neck axis 190 and indicate the amount by which the neck length is affected by each of these trial components. The linear indicia on the neck trial 176 indicate that the neck trial 176 has a minimal effect on the leg length, but have an increased effect on the medial-lateral offset of the resulting joint.

Figure 3:
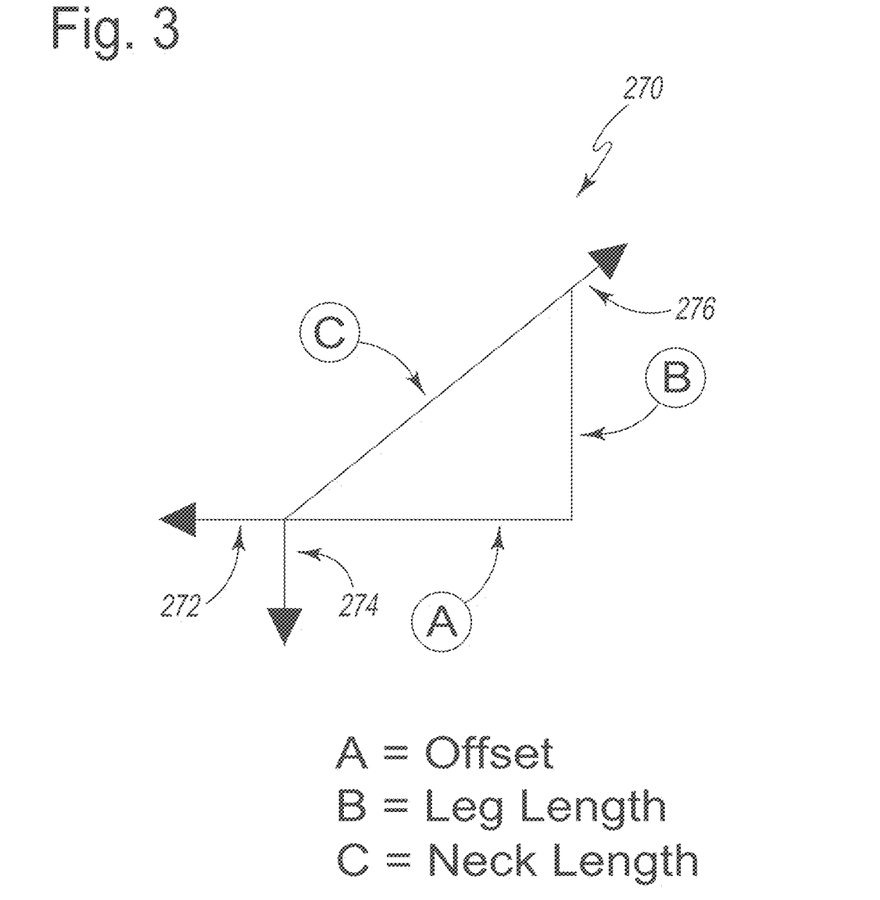
FIG. 3 shows a graphical representation illustrating the effects of the different trail components on the resulting joint.

This is further illustrated in FIG. 3 which shows a graphical representation 270 of the relationship between the linear indicia on the trial components and the changes to the resulting joint.

The number of linear indicia extending in the superior-inferior direction effects the medial-lateral offset of the leg of the patient as illustrated by line A in FIG. 3. The greater the number of vertical lines on the neck trial, the greater the offset of the patient's leg laterally along the medial-lateral axis, as indicated by arrow 272. Similarly, the greater the number of horizontal lines, parallel to the medial-lateral direction, the greater the effect of the neck trial on the leg length of the patient, as illustrated by line B in FIG. 3. The greater the number of lines parallel to the medial-lateral axis, the greater the change in leg length in the inferior direction illustrated by line 274 in FIG. 3.

Further, the number of linear indicia on the liner trial and/or neck trial of the joint, the greater the change in neck length along line C of FIG. 3. FIG. 3 extends generally in the direction of the neck axis 190 and can increase tension in the hip joint in the direction illustrated by line 276 in FIG. 3. As will be appreciated from a comparison of FIGS. 2 and 3, the linear indicia on the head trial 146 and liner trial 114 are generally perpendicular to the direction of the neck axis 190.

If the head trial and/or liner trial are changed to alter the neck length, C, then as illustrated in FIG. 3, this can also have an effect on the leg length, B, and offset, A. For example, reducing the overall neck length has the effect of reducing the offset A and the leg length B. Similarly, increasing the overall neck length has the effect of increasing the offset A and leg length B.

Similarly, increasing the offset A will increase the neck length C slightly, but not necessarily also the leg length B. Similarly, increasing the leg length B will increase the neck length C slightly but may not change the offset A in the medial-lateral direction.

The visual indicia included on the trialling components therefore provides an easily understandable system for allowing the surgeon to immediately understand the contribution which each of the trial components provides to the trial joint in terms of offset and/or leg length and/or neck length. A surgeon can therefore easily determine which one or more of the trial components to change in order to improve the likely outcome of the procedure by visually inspecting the trial components used in the trial joint.

Further, the surgeon can easily determine which of the trial components in the kit to use for a further trial assembly, in order to re-trial the joint with a modified trial joint, using other trialling components from the kit.

Figure 4A:
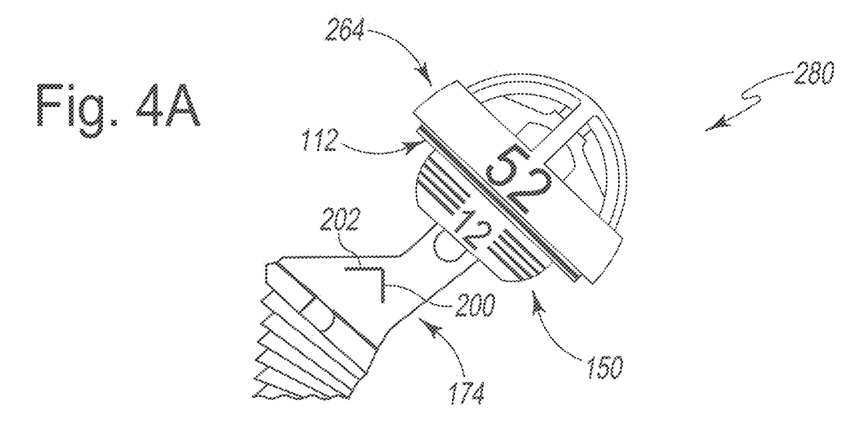
FIGS. 4A to 4C show elevations in the anterior-posterior direction of various trial joints including different assemblies of different combinations of the trial components shown in FIGS. 1A to 1C.

For example, FIG. 4A shows a view in the generally anterior-posterior direction of a right hand hip trial joint 280, similar to that shown in FIG. 2. The trial joint 280 includes trial shell 264, first trial liner 112, fifth trial head 150 and second trial neck 174.

As indicated by the visual indicia 200, 202 on the trial neck 174, the current trial neck 174 has a neutral impact on the leg length and the offset. The single linear indicia on the liner trial 112 shows that the liner trial is providing a minimal contribution to the overall neck length whereas the five linear indicia on the head trial 150 shows that the head trial is contributing significantly to the overall neck length. Hence, if the surgeon wishes to reduce the overall neck length, for example because of significant tension in the soft tissues of the reduced trial joint, then the surgeon may quickly understand, by inspection of the trial joint 280 that the trial head 150 is contributing significantly to the tissue tension.

Figure 4B:
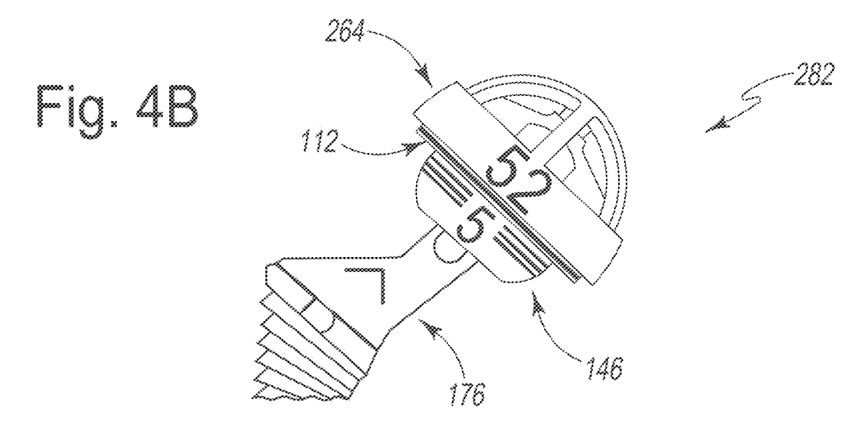

Hence, the surgeon may replace the trial head 150 with the third trial head 146 so as to reduce the overall neck length and resulting in the trial joint 282 illustrated in FIG. 4B.

However, by reducing the overall neck length, along direction C in FIG. 3, the surgeon has now also reduced the offset by moving the leg medially along the medial-lateral axis A. Therefore, the medial-lateral offset of the patient's leg has now been reduced by the trail joint assembly 282 compared to the situation for the trial joint assembly 280 of FIG. 4A. The surgeon may determine that it is desirable to increase the medial-lateral offset laterally. By inspecting the trialling kit 100, the surgeon can immediately see that the third neck trial 176 increases the medial-lateral offset laterally by virtue of the two lines 204, 206 parallel to the inferior-superior axis.

Figure 4C:
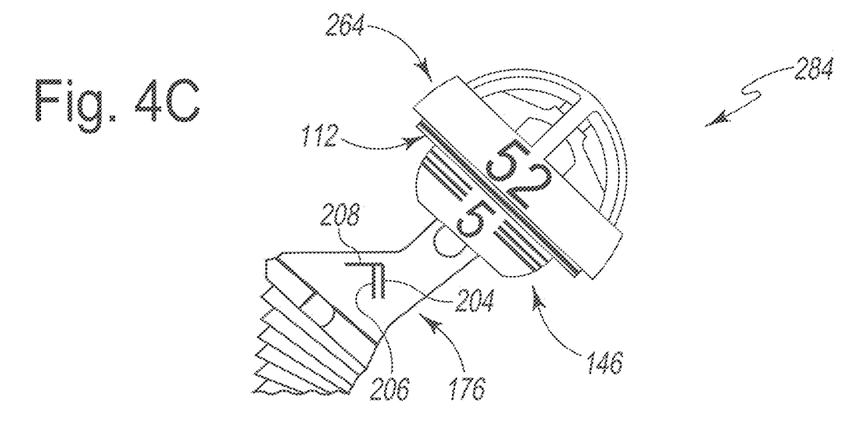

Hence, the surgeon may replace second trial neck 174 with third trial neck 176 so as to arrive at the trial joint 284 illustrated in FIG. 4C. Hence, in the third trial joint 284, the overall neck length has been reduced compared to the first trial assembly 280 and the medial-lateral offset increased by the third neck trial 176 so as to better reproduce the intended medial-lateral offset and to compensate for the reduction in medial-lateral offset by the use of the third head trial 146 in the place of the fifth head trial 150 to reduce the overall neck length.

As can be seen in FIGS. 4A to 4C, the number of linear indicia generally perpendicular to the neck axis (those on the liner trial and the head trial) are representative of the amount of tension in the trial joint. The number of linear indicia extending in the inferior-superior direction are generally indicative of the amount of offset of the trial joint. The number of linear indicia in the medial-lateral direction are indicative of the amount of leg length in the trial joint. Hence, the linear indicia provide an easy to see and simple to understand indication of the effect of each of the different trialling components on the likely surgical outcome for such a hip joint.

Furthermore, not only do the linear indicia allow the surgeon to understand which trialling components are contributing what effect to the hip joint, the surgeon can also use the visual indicia to easily and accurately determine which of the other trial components to select to use to retrial the joint in order to correct for any undesirable properties of the current trial, e.g. in terms of offset, leg length and/or tissue tension. This will be explained in greater detail with reference to FIG. 5.

Figure 5:
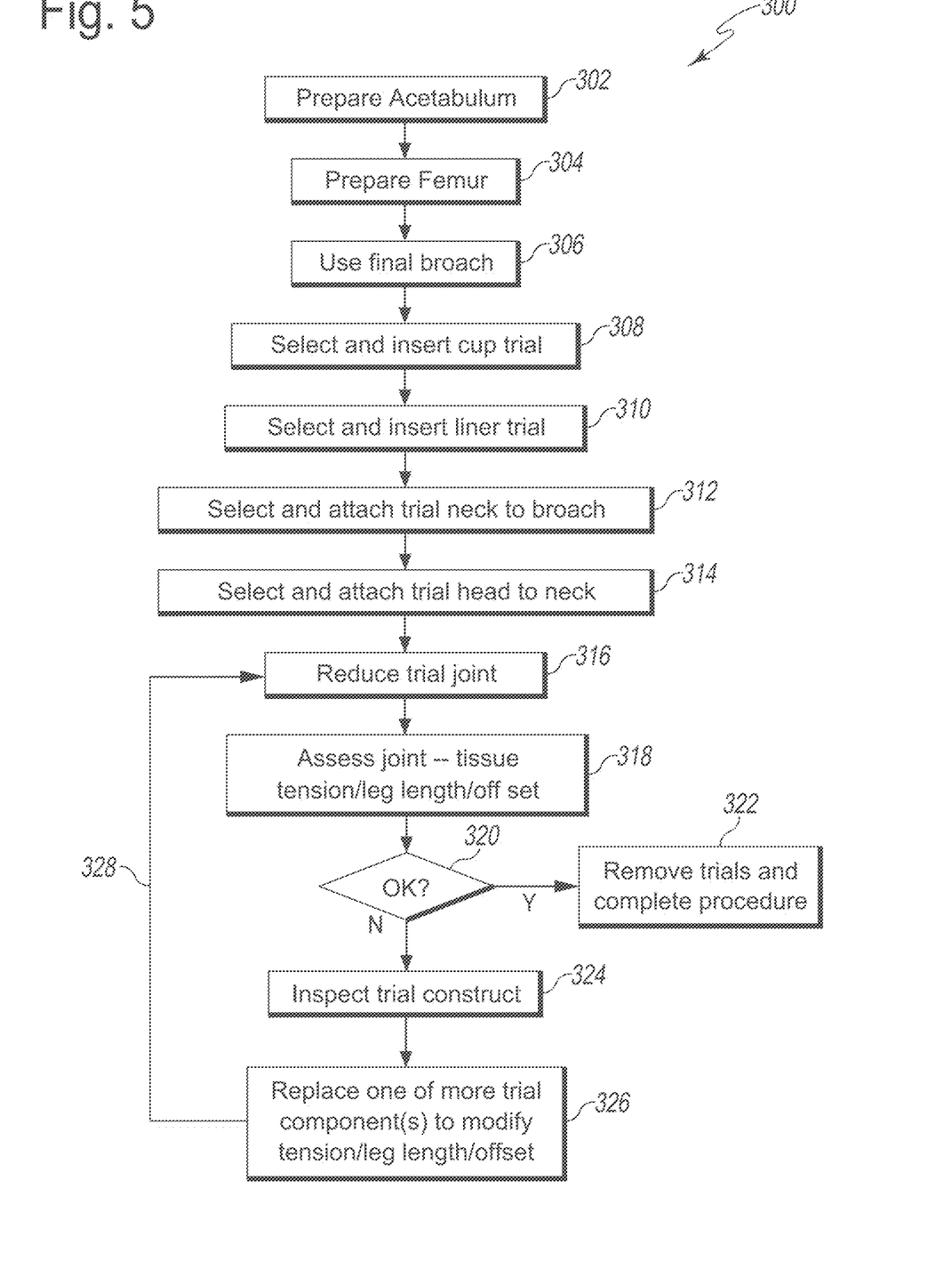
FIG. 5 shows a flow chart illustrating a method of using the trial components according to an aspect of the invention.

FIG. 5 illustrates a flow chart illustrating a method 300 of using the trialling kit 100 according to a further embodiment of the invention. A number of the steps of the surgical procedure for replacing a hip joint are generally known, and are not described in detail so as not to obscure the present invention. The present invention is particularly relevant to the trialling stage of a hip replacement surgical procedure.

The method 300 begins with preparation of the acetabulum at 302. This may include removing the various soft tissue structures surrounding the acetabulum and using an acetabular grater and/or reamer in order to prepare a substantially hemispherical cavity within the acetabulum of the patient's pelvis.

At 304, the femur of the patient is prepared. This can include resecting the femoral head and the proximal part of the femur. Various tools and instruments commonly known in the art may be used to initiate and prepare an intramedullary cavity extending generally along the proximal part of the femoral axis. At some stage in the preparation of the femur, a final size broach may be used 306 to finally prepare the femoral cavity. A handle may then be removed from the broach and the broach may be left within the femur. For example, broach 260 is shown in FIG. 2.

At 308, according to a planned surgical procedure, a cup trial, e.g. trial 264, may be selected and inserted in the prepared acetabular cavity. At step 310, a liner trial can be selected from the trialling kit which corresponds to the pre-planned cup and head size for the patient. If the cup trial has been inserted with a significant vertical orientation or there is a risk of the patient dislocating, then augmented liner 114 may be used. Otherwise, the surgeon may select a standard liner trial for insertion in the cup trial.

At 312, a one of the neck trials 170 can be selected in accordance with the pre-planned surgical procedure and releasably attached to the broach 260 at step 312.

At 314, a selected one of the head trials 140 can be selected and attached to the taper of the neck trial at 314. Then at 316 the trial joint can be reduced and has the general structure illustrated in FIGS. 2 and 4A to 4C.

At 318, the surgeon can assess the properties of the resulting trial joint. This can include assessing the tension in the soft tissues of the hip joint. This may also include assessing the resulting leg length of the patient, along the generally inferior-superior axis of the patient. This may also include assessing the offset of the patient's leg along the medial-lateral axis. Step 318 may also include carrying out a range of motion (ROM) assessment to determine any likely impact between the trial components and also to assess the tissue tension arising from the currently selected trial components. At step 320, the surgeon may determine, based on experience or other factors, whether the hip joint arising from this selection of components is acceptable or not. If it is acceptable, then at 322, the trial components can be removed. The trial components can then be replaced with prosthetic components having generally the same size, position and/or orientation as the trial components.

Alternatively, the surgeon may select prosthetic components having slightly different geometries to compensate for any properties of the hip joint determined during the assessment stage 318 instead of selecting prosthetic components identical to the trial components. For example, if the surgeon determines at 318 that the tissue tension is slightly too great, than at 322, the surgeon may select to use a slightly shorter neck length for the femoral prosthesis in order to help reduce the tissue tension.

Figure 6:
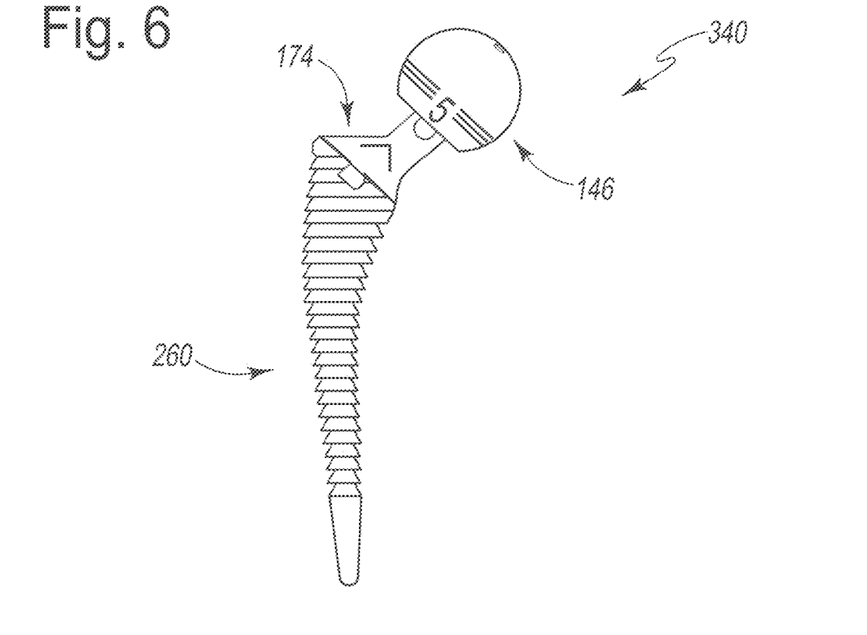
FIGS. 6, 7 and 8 show elevations in the anterior-posterior direction of various trial joints including different assemblies of different combinations of the trial components of FIGS. 1A to 1C that may be used during the method illustrated in FIG. 5.

Returning to step 320, if the surgeon determines that the joint is not acceptable in some way, then at 324, the surgeon can inspect the trial joint in situ. For example, if at 318, the surgeon assesses the joint and determines that the tissue tension is too loose and also the medial-lateral offset is too small for the current trial assembly then the surgeon can inspect the trial construct at 324 to determine how the trial construct might be modified. For example, FIG. 6 shows a view of a trial assembly 340 comprising the third head trial 146 mounted on the second neck trial 174 mounted on femoral broach 260. As can be seen from the number of linear indicia on the head trial 146, the head trial is contributing a moderate amount to the overall neck length and, from the linear indicia on the neck trail 174, the neck trial 174 is contributing neutral amounts to the leg length and offset. Hence, the surgeon can easily understand how the current trial components are impacting on the trial joint performance.

Hence, at 326, the surgeon can separate the trial joint and select one or more trial components from the trialling kit 100 in order to rectify the surgical outcome. For example, if the surgeon considers that the tissue tension is slightly too loose and the medial-lateral offset is too small, the surgeon can easily determine, from inspecting the trialling kit 100 which of the other neck trials can be used to increase the medial-lateral offset but without increasing the leg length. As noted above, increasing the medial-lateral offset will also increase the overall neck length slightly. Hence, at 326, the surgeon may disassemble the initial trial assembly 340 and replace neck trial 172 with the third neck trial 176 to arrive at the trial assembly 350 illustrated in FIG. 7.

Figure 7:
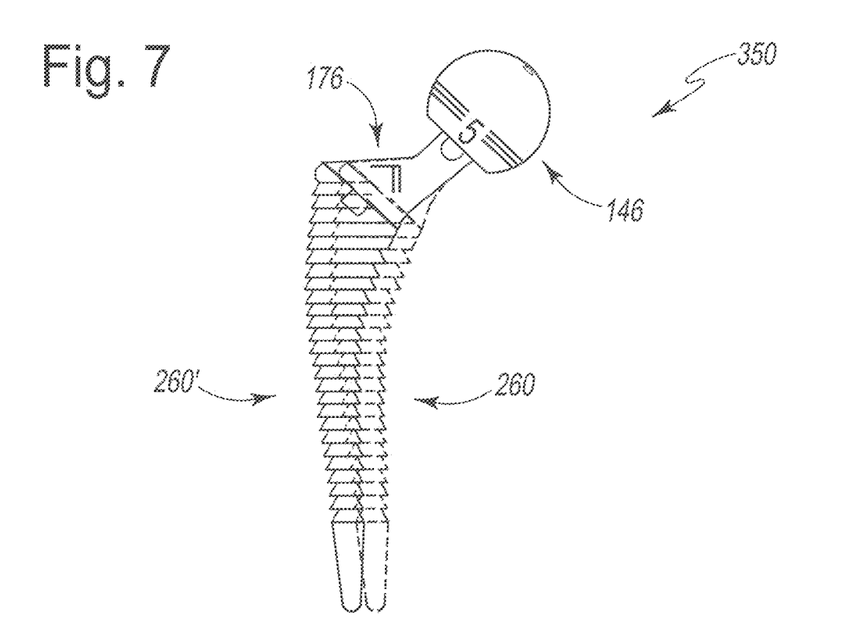

Hence, process flow can return as illustrated by process flow line 328 to step 316 at which the surgeon can reduce the trial joint with the new trial assembly 350. The effect of replacing neck trial 174 with neck trial 176 is illustrated in FIG. 7. The previous position of the femoral broach 260 is indicated in shadow and the new position of femoral broach is indicated in darker form 260'. Hence, the effect of replacing neck trial 174 with neck trial 176 is to move the patient's leg laterally along the medial-lateral axis by increasing the offset by about 7 mm, but while maintaining the leg length. In FIG. 7, the linear indicia on the anteriorly facing surface of the neck trial 176 indicate that the neck trial has the effect of moving the patient's leg laterally relative to the centre of rotation of the hip joint.

Hence, the reduced replacement trial joint 350 can be assessed again at step 318 and the surgeon may determine that the second trial hip joint 350 is likely to lead to a satisfactory surgical outcome and therefore may be adopted for the final prosthetic implants.

Figure 8:
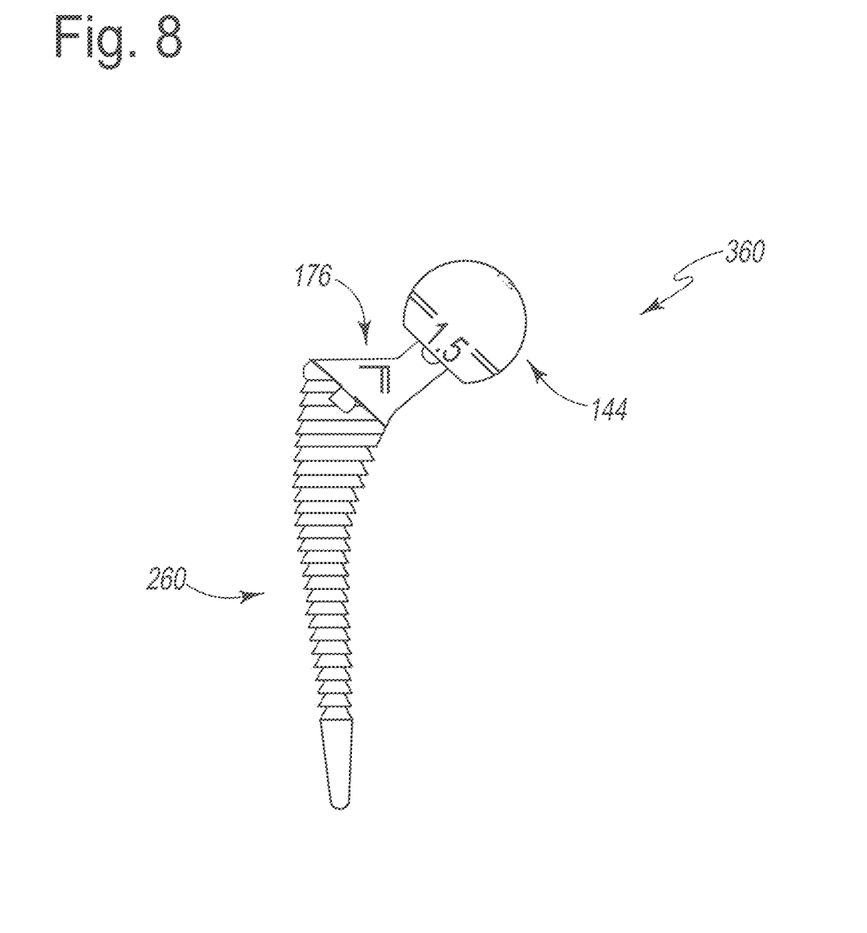

As another example, returning to step 318, if it were determined at 318 that the tissue tension were too great and the medial-lateral offset were too small at 318 for the initial trial assembly 340, then at 324, the surgeon can immediately understand from the linear indicia on the initial trial head 146 that the trial head is contributing significantly to the neck length and therefore to the tension. Hence, at 326, the surgeon may easily determine that a trial head which reduces the tissue tension could be tried and can easily identify, e.g., the second trial head 144 owing to the reduced number of linear indicia thereon. The surgeon can also easily identify that trial neck 176 may be considered as that will increase the medial-lateral offset (two vertical lines 204, 206) without changing the leg length (one horizontal line 208). Hence, the surgeon may select the second trial head 144 and the third trial neck 176 and assemble trial assembly 360 as illustrated in FIG. 8.

Process flow returns as indicated by line 328 to 316 and the trial joint can be reduced again and further assessed at 318. The surgeon may then determine that the tissue tension is now appropriate and also that the offset is appropriate at 320. As illustrated in FIG. 8, the second head trial 144 has the effect of reducing the overall neck length while the third neck trial 176 has the effect of increasing the offset laterally, without changing the leg length, and slightly contributing to the overall neck length.

Further, the angle between the linear indicia on the liner trial and the linear indicia of the head trail can be used to help assess whether an augmented liner trial might be used. For example, assuming a neutral liner trial is currently being used, then during the assessment at 318, the surgeon may place the femur in the Ranawat sign position (generally the operated leg is placed in extension and internally rotated by 45°). The surgeon may then assess whether the linear indicium on the liner trial are sufficiently parallel to the linear indicia on the head trial. If they are, for example because the acute angle subtended between them is less than a few degrees, for example less than about 10°, then the surgeon may determine that the risk of dislocation is low and select to use a normal liner. Alternatively, if the acute angle subtended between them is greater than about 10°, for example, then the surgeon may determine that the risk of dislocation is high and the surgeon may select to use an augmented liner instead. Hence, the linear indicia of tension in the joint can also be used to assess the risk of dislocation and hence whether to use an augmented liner or not.

Hence, the number of linear indicia in the first and second directions on the neck trial indicate the amount to which the neck trial contributes to the position of the patient's leg in the offset and leg length directions. The number of linear indicia on the head trial and/or liner trial are representative of the amount by which these components contribute to the neck length. Therefore, the surgeon can easily understand by visual inspection how each of the different trial components are contributing to the behaviour of the trial joint simply by inspecting them in situ.

Further, the linear indicia can easily be used to select a one or more replacement trial components in order to compensate for any potential deficiencies in a current trial joint and allow a further trial assembly to be assembled likely to reduce any deficiencies in the joint.

Further, as the liner trials and head trials of any particular head size are colour coded, a surgeon can easily ensure that the trial head size and trial liner size match for any trialling kit. Hence, if a trialling kit is provided with liner trials and head trials of different sizes, such that a surgeon decides to use a different sized liner trial, then the surgeon can easily determine which head trials match the different sized liner based on their matching colours.

In this specification, example embodiments have been presented in terms of a selected set of details. However, a person of ordinary skill in the art would understand that many other example embodiments may be practiced which include a different selected set of these details. It is intended that the following claims cover all possible example embodiments.

Any instructions and/or flowchart steps can be executed in any order, unless a specific order is explicitly stated or implicitly required. Also, those skilled in the art will recognize that while one example set of instructions/method has been discussed, the material in this specification can be combined in a variety of ways to yield other examples as well, and are to be understood within a context provided by this detailed description.

While the disclosure is amenable to various modifications and alternative forms, specifics thereof have been shown by way of example in the drawings and described in detail. It should be understood, however, that other embodiments, beyond the particular embodiments described, are possible as well. All modifications, equivalents, and alternative embodiments falling within the scope of the appended claims are covered as well.

What is claimed is:

1. A neck trial comprising:
   a body having an exterior surface; and
   a straight neck extending away from the body and along a neck axis, a taper provided at a free end of the neck for releasably attaching a head trial thereto in use;
   wherein:
   at least one first line is provided on the exterior surface of the body and the or each first line extends in a first direction parallel to an inferior-superior axis of a patient when the neck trial is in use and at least one second line is provided on the exterior surface of the body and the or each second line extends in a second direction parallel to a medial-lateral axis of the patient when the neck trial is in use, and wherein:
   the number of first lines, or the position of the first line or lines relative to the second line or lines, is indicative of an amount of offset of the patient's leg in the medial-lateral direction caused by the neck trial in use; and
   the number of second lines, or the position of the second line or lines relative to the first line or lines, is indicative of an amount of leg-length of the patient's leg in the inferior-superior direction caused by the neck trial in use.

2. The neck trial as claimed in claim 1, wherein the number of first lines is in the range from 1 to 3.

3. The neck trial as claimed in claim 1, wherein the number of second lines is in the range from 1 to 3.

4. The neck trial as claimed in claim 1, wherein the number of first lines is greater than one and the number of second lines is greater than one.

5. The neck trial as claimed in claim 1, wherein each line is a solid line.

6. The neck trial as claimed in claim 1, wherein all of the first lines and the second lines are adjacent and positioned on the same part of the exterior surface.

7. The neck trial as claimed in claim 1, wherein all of the first lines and second lines are on an anterior facing surface or a posterior facing surface of the neck trial in use.

8. The neck trial as claimed in claim 1, wherein the or each first line is separate from the or each second line.

9. The neck trial as claimed in claim 1, wherein the or each first line is connected to the or each second line.

10. The neck trial as claimed in claim 1, wherein the or each first line is positioned medially to the or each second line.

11. The neck trial as claimed in claim 1, wherein the or each first line is positioned laterally to the or each second line.

12. The neck trial as claimed in claim 1, wherein the or each second line is positioned superiorly to the or each first line.

13. The neck trial as claimed in claim 1, wherein the or each second line is positioned inferiorly to the or each first line.

14. A trial assembly, comprising:
   a neck trial comprising:
      a body having an exterior surface; and
      a straight neck extending away from the body and along a neck axis, a taper provided at a free end of the neck for releasably attaching a head trial thereto in use, wherein at least one first line is provided on the exterior surface of the body and the or each first line extends in a first direction parallel to an inferior-superior axis of a patient when the neck trial is in use and at least one second line is provided on the exterior surface of the body and the or each second line extends in a second direction parallel to a medial-lateral axis of the patient when the neck trial is in use, and wherein:
      the number of first lines, or the position of the first line or lines relative to the second line or lines, is indicative of an amount of offset of the patient's leg in the medial-lateral direction caused by the neck trial in use; and
      the number of second lines, or the position of the second line or lines relative to the first line or lines, is indicative of an amount of leg-length of the patient's leg in the interior-superior direction caused by the neck trial in use; and
   a head trial, wherein the head trial is releasably attached to the neck trial and has at least one head line, the or each head line extending in a respective plane perpendicular to the neck axis, and wherein the number of head lines is indicative of the length of the trial assembly along the neck axis.

15. The trial assembly of claim 14, and further comprising:
   a liner trial, wherein the liner trial has a rim defining a mouth of the liner trial, the head trial being accepted in the mouth, and wherein a liner line extends in a plane parallel to the mouth.

* * * * *